US006632647B2

(12) United States Patent
Hirth-Dietrich et al.

(10) Patent No.: US 6,632,647 B2
(45) Date of Patent: Oct. 14, 2003

(54) **USE OF STRAINS OF *PARAPOXVIRUS OVIS* AGAINST ORGAN FIBROSIS**

(75) Inventors: Claudia Hirth-Dietrich, Wuppertal (DE); Tobias Schlapp, Cologne (DE); Angela Siegling, Paris (FR); Andreas Knorr, Erkrath (DE); Olaf Weber, Woodbridge, CT (US); Gudrun Theiss, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/903,005

(22) Filed: Jul. 11, 2001

(65) Prior Publication Data

US 2002/0076418 A1 Jun. 20, 2002

(30) Foreign Application Priority Data

Jul. 11, 2000 (DE) .......................................... 100 33 581
May 8, 2001 (DE) .......................................... 101 22 233

(51) Int. Cl.⁷ .................................................. C12N 7/08
(52) U.S. Cl. .................... 435/235.1; 435/237; 424/93.1; 424/93.6; 424/281.1
(58) Field of Search ............................. 435/235.1, 237; 424/281.1, 93.1, 93.6

(56) References Cited

U.S. PATENT DOCUMENTS

| 4,191,745 | A | * | 3/1980 | Mayr et al. |
| 4,360,510 | A | * | 11/1982 | Proctor |
| 4,663,306 | A | * | 5/1987 | Cantrell |
| 5,094,850 | A | * | 3/1992 | Mayr et al. |
| 6,162,600 | A | * | 12/2000 | Mayr |

FOREIGN PATENT DOCUMENTS

| DE | 4405841 C1 | * | 2/1995 |
| DE | 3504940 | | 6/1997 |
| DE | 19922407 A1 | * | 11/2000 |
| EP | 0669133 | | 8/1995 |
| JP | 405271067 A | * | 10/1993 |
| WO | 9522978 | | 8/1995 |
| WO | WO 97/38724 | * | 10/1997 |

OTHER PUBLICATIONS

Bhunchet, E., Wake, K., "Role of Mesenchymal Cell Populations in Porcine Serum–induced Rat Liver Fibrosis", Hepatology, 16: 1452–1473 (1992).

McLean, E. , McLean, A., Sutton, P., "Instant Cirrhosis, An Improved Method For Producing Cirrhosis of the Liver in Rats by simultaneous Administration of Carbon Tetra–Chloride and Phenobarbitone", Br. J. exp. Path., 50: 502–506 (1969).

* cited by examiner

Primary Examiner—Leon B. Lankford, Jr.
(74) Attorney, Agent, or Firm—Susan M. Pellegrino

(57) ABSTRACT

The present invention relates to the use, in humans, of inactivated parapoxviruses for the prophylaxis and treatment of diseases which are accompanied by an increased deposition of collagen, with it being possible for both internal organs, such as the liver, and the skin and its appended structures, to be affected. The invention relates, in particular, to liver fibrosis and/or liver cirrhosis consequent upon virus hepatitis, or to ethanol-induced liver diseases and to cystic fibrosis.

12 Claims, No Drawings

USE OF STRAINS OF *PARAPOXVIRUS OVIS* AGAINST ORGAN FIBROSIS

The present invention relates to the use in humans of inactivated parapoxviruses in the prophylaxis and treatment of diseases which are accompanied by increased deposition of collagen, in connection with which both internal organs, such as liver, and the skin and its appended structures can be affected. The invention relates, in particular, to liver fibrosis and liver cirrhosis following viral hepatitis, or ethanol-induced liver diseases, and also cystic fibrosis.

The present invention relates, in particular, to the use in humans of isolates of *Parapoxvirus ovis*, for example the strains D1701, orf-11, Greek orf strain 176, Greek orf strain 155, New Zealand (NZ) isolates, e.g. NZ2, NZ7 and NZ10, and also Baypamun®, which is derived from D1701.

In addition to the starting strains, the invention also relates to the descendants which are obtained by passaging and/or adaptation to particular cells, for example WI 38. In addition to the complete viruses, the invention also relates to parts or fragments of these viruses. Parts are to be understood as being genomic or subgenomic fragments which are expressed using suitable vectors, for example vaccinia, in suitable systems such as fibroblast cell cultures. Fragments are understood as being the fractions which are obtained by biochemical purification, such as chromatography, or the particles which are obtained after using physical methods, such as disruption by means of sonication.

It is known that Parapoxvirus can stimulate the nonspecific immune reaction in vertebrates. Baypamun®, which is a preparation of chemically inactivated *Parapoxvirus ovis*, strain D1701, is used for the prophylaxis, metaphylaxis and therapy of infectious diseases and for preventing stress-induced diseases in animals.

While the patent DE 3 504 940 A (Mayr, Anton) teaches the favourable effect of Baypamun® in conditions such as immunoinsufficiency induced by energy-rich irradiation, chemotherapy, AIDS, immunosuppression, age-associated damage and detoxifying effects, it does not teach the immediate reduction of liver fibrosis. DE 3 504 940 also teaches that Baypamun® supports the efficacy of a tumour therapy as an adjunct and that it detects newborn children from diseases caused by inadequate maternal immune defence.

Taking the present state of knowledge as the starting point, it has now been found, surprisingly, that administration of inactivated parapoxviruses can reduce or prevent liver fibrosis. In animal models, this effect has been found in the case of carbon tetrachloride-induced liver fibrosis, which is based on toxic liver damage, and in the case of liver fibrosis which is induced by heterologous serum and in which there is no liver inflammation. The extent of the therapeutic effect is also surprising: the excessive production of collagen which is associated with liver fibrosis is inhibited by 60% in the carbon tetrachloride model, while it is almost completely inhibited in the serum model. In agreement with these results from long-term experiments, it was then possible to demonstrate, from acute administration of carbon tetrachloride, that Baypamun® and the preparation obtained from the abovementioned *Parapoxvirus ovis* strains inhibit the transformation of the hepatic stellate cells into the collagen-producing myofibroblast type.

While liver fibrosis and/or liver cirrhosis can be induced by different noxas, such as viral infections and alcohol abuse, the different pathomechanisms enter a common final path, i.e. collagen production. As the animal experiment results from the above-described non-infectious models demonstrate, the administration of inactivated parapox viruses surprisingly prevents collagen deposition independently of the inducing noxa.

Parapoxviruses therefore open up a novel therapeutic principle for exerting an effect on the final path which is common to all the diseases leading to fibrosis.

This effect suggests that, when parapoxvirus preparations are used, a particularly effective therapy will be achieved, even in the case of virus-induced liver fibrosis, since it is known that such preparations possess additional immuno-stimulatory effects.

The powerful antifibrotic effect of Baypamun® which has now been found opens up the possibility of employing Baypamun® or preparations of NZ2 as the reference standard for assessing antifibrotic effects in assays for identifying antifibrotic substances.

Inactivated parapoxviruses or their descendants, and preparations obtained from the above strains, consequently possess an all-embracing antifibrotic spectrum of activity and are therefore suitable not only for the prophylaxis and therapy of fibrotic diseases of the liver but also in connection with fibrotic diseases of other organs, for example of the lungs, the pancreas, the heart and the skin. Particular preference is given to using isolates of parapoxviruses in the prophylaxis and treatment of liver fibrosis and liver cirrhosis.

Depending on the clinical problem, the parapoxvirus-based therapeutic agent is administered systemically, that is, for example, intramuscularly, subcutaneously, intraperitoneally, intravenously, orally or by inhalation, or else locally. The parapoxvirus is then present purified and lyophilized, and is suspended in a suitable solvent immediately prior to administration, or is present in another suitable formulation, or is present in a gastric juice-resistant oral administration form or some other oral administration form.

In this connection, several administrations, or long-term treatment in accordance with chronological schemes which correspond to the requirements of the clinical problem, may be necessary.

The present invention relates to the use of isolates of parapoxviruses, which are obtained from the strains D1701, orf-11, Greek orf strain 176, Greek orf strain 155, and the New Zealand (NZ) strains, for producing medicaments which have a preventive or curative effect on organ fibroses in humans. Preference is given to using New Zealand (NZ) strains, i.e. the strains NZ2, NZ7 and NZ10, for producing medicaments which have a preventive or curative effect on organ fibroses in humans, with the strain NZ2 being particularly preferred. In addition to this, the above-described parapoxviruses can be modified by passaging or adaptation to suitable cells, and those parapoxviruses which have been obtained by passaging or adaptation can be used for producing medicaments which have a preventive or curative effect on organ fibroses in humans, in connection with which it is possible to use human cells, such as WI-38, MRC-5, bovine cells, such as BK-K13A47/Reg or MDBK, and ovine cells, such as MDOK, for example, for the passaging or adaptation. It is also possible to use parts or fragments of the abovementioned parapoxviruses for producing medicaments which have a preventive or curative effect on organ fibroses in humans. Parts are understood as being genomic or sub-genomic fragments which are expressed in suitable systems, such as fibroblast cell cultures, using suitable vectors, such as vaccinia viruses, and fragments are understood as being the fractions, which are obtained by biochemical purification, such as chromatography, of the viral particles which are expressed or which are physically disrupted, for example by the influence of ultrasonication. The invention furthermore relates to the use of the above-described *Parapoxvirus ovis* strains, or of the modifications which are obtained therefrom as described above, in combination with other agents for producing medicaments and medicament preparations which have a preventive or curative effect on organ fibroses in humans, and to the use of Baypamun®, on its own or in combination with other agents, for producing medicaments and medicament preparations which have a preventive or curative effect on organ fibroses in humans. The invention preferably relates to the use of the above-described *Parapoxvirus ovis* strains, or of the modifications which are obtained therefrom as described above, in combination with other agents in a formulation for oral administration, for example in gastric juice-resistant capsules.

The invention furthermore relates to the use of Baypamun® or preparations of NZ2 as a reference for assessing antifibrotic effects in assays for identifying antifibrotic substances.

EXAMPLE 1

Effect of *Parapoxvirus ovis*, Strain D 1701, Baypamun®

Methodology

Baypamun®, dry substance, a preparation isolated from chemically inactivated *Parapoxvirus ovis*, strain D 1701, was dissolved in water for injection as directed (titer based on the TCID50 (50% tissue culture infective dose) approx. $10^7$ per ml).

A Polygeline solution, having the same content of protein as in the Baypamun® solution, was administered to the control group animals as a placebo solution.

0.5 ml of solution was administered i.p. per animal and administration. The administration was performed three times per week but never on consecutive days.

Baypamun® was tested in two animal models in which the origin of the fibrosis differed, i.e. in the carbon tetrachloride model and in the pig serum model.

Chronic treatment with carbon tetrachloride is a standard method for experimentally inducing liver fibrosis with subsequent cirrhosis (McLean E K, McLean A E M, Sutton P M. Instant cirrhosis. Br. J Exp. Pathol. 1969; 50: 502–506). It is recognised generally as being a model for human liver fibrosis and liver cirrhosis. Female Sprague-Dawley rats were used. In order to ensure maximal induction of the microsomal metabolism of carbon tetrachloride, the animals were given 1 g of isoniazide/l with the drinking water one week before the beginning of the treatment. Carbon tetrachloride was given orally every fifth day at a dose of 0.1 ml/100 g of body weight (carbon tetrachloride:mineral oil=1:1). After seven weeks of treatment, the animals were sacrificed and examined. The treatment with Baypamun® was carried out in parallel with the carbon tetrachloride treatment.

Treatment with heterologous serum, for example pig serum in the case of rats, is likewise a method which is frequently employed in the literature for inducing liver fibrosis with subsequent cirrhosis, with this method, in contrast to other models, only causing minimal damage to, and inflammation of, the liver parenchymal cells (Bhunchet, E. and Wake, K. (1992): Role of mesenchymal cell populations in porcine serum-induced rat liver fibrosis. Hepatology 16: 1452–1473). Female Sprague Dawley rats were treated 2×weekly i.e. with 0.5 ml of sterile pig serum (Sigma)/animal, with the control animals being given sterile physiological sodium chloride solution (2×weekly, 0.5 ml/animal i.p.). The treatment with Baypamun® was carried out in parallel with the pig serum treatment but never on the same day. After seven weeks of treatment, the animals were sacrificed and the livers were removed for quantifying the content of collagen.

For examining the liver tissue histologically, standardized transverse tissue cylinders (approximately 10×2 mm) were punched out from the right anterior lobe of the liver. Frozen sections were stained with 0.1% Picrosirius red solution for detecting scar collagen produced by the liver fibrosis.

Fast Green was used as a counterstain for contrast amplification. The extent of the liver fibrosis was determined in each section as the percentage fraction of the total area measured represented by the Picrosirius red-stained area. The parameters of the videomicroscopic colour detection were standardized and kept constant throughout the experiment. 64 squares in a standardized 31 $mm^2$ grid were measured at 50-fold final magnification.

In order to quantify the extent of the transformation of hepatic stellate cells (HSC; also Ito cells or vitamin A storage cells) following acute treatment of rats with carbon tetrachloride, the α-smooth muscle activ-positive cells were detected immunohistochemically. The α-smooth muscle activ-positive area was ascertained, at 200-fold final magnification, in each section in each case in 16 centrilobular 248×180 μm fields. The transformation of HSC into collagen-producing and growth factor-producing myofibroblast-like cells is known to be the crucial step in the induction of liver fibrosis. Transformed HSC are therefore an early indicator of fibrogenic activity in the liver.

A Leica Quantimed 500MC (Leica Germany) was used for the semiautomatic morphometry.

In order to determine OH-proline, 50–100 mg of liver tissue were in each case dried and boiled for approx. 17 hours with 6N HCl. After evaporating off the acid in a vacuum-drying oven, the residue was dissolved in 5 ml of distilled water and this solution was filtered. 200 μl of the filtered solution were incubated, at room temperature for 25 min, with 200 μl of ethanol and 200 μl of oxidation solution (7% aqueous chloramine T hydrate solution, diluted 1:4 with acetate-citrate buffer pH 6.0). After that, 400 μl of Ehrlich's reagent (12 g of 4-dimethylaminobenzaldehyde in 20 ml of ethanol+2.74 ml of concentrated sulphuric acid in 20 ml of ethanol) were added. After incubation at 35° C. for 3 hours, the absorption was measured at 573 nm. Aqueous OH-proline (Sigma) solutions were used for the standard series. The content of OH-proline in the liver samples was calculated in mg per g of liver dry weight.

In order to monitor the formation of reactive oxygen free radicals, the concentration of reduced α-tocopherol (α-TOC), a free radical-capturing agent, was measured in the liver, while the activity of the free radical-sensitive enzyme 7-ethoxyresorufin deethylase (EROD) was measured in the serum. Both parameters are characteristically down-regulated in association with carbon tetrachloride poisoning and enable the severity of the oxidative damage to the tissue to be estimated.

The liver status of the animals was determined by measuring some standard serum parameters:

alanine aminotransferase (ALT), alkaline phosphatase (AP), aspartate amino-transferase (AST), γ-glutamyl transferase (GGT), glutamate dehydrogenase (GLDH), and total bilirubin (TBIL).

Results:

Treatment with Baypamun® significantly decreases the extent of the fibrotic degeneration of the livers of carbon tetrachloride-treated rats (FIG. 1). In addition, an almost complete inhibition of the HSC transformation can be observed (FIG. 2). The number of proliferating non-parenchymal cells in the livers of Baypamun®-treated animals is markedly reduced (FIG. 3). Non-parenchymal cells include HSC and the Kupffer cells which are likewise involved in the fibrogenesis.

The serum indicators of hepatocellular damage, such as ALT, AP, AST, GGT, GLDH and TBIL (Table 1), show a tendency to normalization.

The same decrease in EROD and α-tocopherol concentrations in the control group and in the Baypamun®-treated group provides evidence of the presence of toxic reactive oxygen free radicals resulting from the carbon tetrachloride poisoning in both groups (Tables 1 and 2). The possibility of the "antifibrotic" effect of Baypamun® being due to a detoxification effect can therefore be ruled out.

In the serum model, Baypamun® exhibits almost complete suppression of the fibrosis (FIG. 4): In the Baypamun®-treated rats, both the content of hydroxyproline and the sirius red-stainable area in the livers are virtually at levels seen in the healthy control animals, whereas they are increased severalfold in the serum-treated control rats. In the Baypamun group, the increase in collagen content which is induced by the pig serum treatment is only 10% of the corresponding value in the control group.

EXAMPLE 2

*Parapoxvirus ovis*, Strain NZ 2

Methodology:

NZ2 virus was replicated in tank stacks. For this, BK clone 3A cells were cultured for 3 to 5 days in cell culture dishes (37° C.) in EMEM 2 gr+10% FCS until the cell lawn was 90 to 100% confluent. Four cell culture dishes were used as inoculum for each tank stack and the latter was filled with medium (EMEM 2 gr+10% FCS) to a volume of 2.5 liters. After incubating at 37° C. for from 3 to 5 days (90 to 100% confluent cell lawn), the medium was replaced with EMEM 2 g without added serum and the culture was infected with NZ2 virus (MOI, 0.001 to 0.01).

After 100% CPE had been reached (incubation at 37° C. for approx. 7 to 8 days), the virus was harvested. For this, the virus suspension was aliquoted into sterile media bags and frozen at −80° C. The suspension was subsequently thawed at 37° C. in an incubation room and freed of cells by means of deep-bed filtration (pore size 5 μm). After this, the virus suspension was concentrated by a factor of 20 to 40 by means of ultrafiltration (100 kDa cutoff). As an alternative, the virus can be concentrated by ultracentrifugation (Ti45, 30,000 rpm, 4° C., 60 min).

The titre, as achieved by the concentration, of the virus present in the suspension was determined by means of titrating on BK clone 3A cells. After the virus titre had been adjusted to 6.0 using EMEM medium without FCS, the virus was then heat-inactivated at 58° C. for 2 h. The inactivation was checked by means of an inactivation control performed on BK clone 3A cells.

*Parapoxvirus ovis*, strain NZ2 was investigated in the model, already used in Example 1, of pig serum-induced liver fibrosis in rats:

Female Sprague Dawley rats were treated i.p. 2×weekly with 0.5 ml of sterile pig serum (Sigma)/animal, while control animals were treated with sterile physiological sodium chloride solution (2×weekly, 0.5 ml/animal i.p.). Strain NZ 2 was administered i.p. 3×weekly in doses of $1.5\times10^5$ and $5.0\times10^5$ $TCID_{50}$/animal, respectively (administration volume: 0.5 ml/animal). For the lower dose, the starting material was diluted with cell culture medium (Eagle's minimum essential medium, Sigma). Control animals were treated with cell culture medium. While the treatment with strain NZ 2 took place in parallel with the serum treatment, it was never given on the same day. After 7 weeks of treatment, the animals were killed and the livers were removed; the liver fibrosis was then quantified both morphometrically and by way of the content of OH-proline. The methodology for this has already been described in Example 1.

Results:

The results of the collagen determination are depicted in FIG. 5. Surprisingly, the treatment with strain NZ 2 is able to suppress the development of liver fibrosis: in comparison with healthy animals, the serum-treated control animals exhibit a marked increase in the content of OH-proline and in sirius red-stainable collagen. This increase is reduced by NZ 2 in a dose-dependent manner. The extent of the effect is also surprising: the $5\times10^5$ $TCID_{50}$ dose reduces the increase in the content of collagen in the liver to less than 10% of the control value. A qualitative assessment of the histological preparations showed that the proportion of animals having collagen septa is reduced from 93% (14/15) down to 33% (5/15) in the $1.5\times10^5$ $TCID_{50}$ group and down to 0% in the $5.0\times10^5$ $TCID_{50}$ group.

EXAMPLE 3

Antifibrotic Effect of PPVO Following Oral Administration

PPVO was formulated as a dry lyophilisate in gastric juice-resistant capsules (Elanco, Ind., USA).

Four groups of in each case six experimental animals were treated as follows: One control group (group 1) was given only a gastric juice-resistant capsule (without PPVO), which was administered orally, with sterile sodium chloride solution (0.5 ml/animal) being additionally injected i.p. In group 2, a gastric juice-resistant capsule (without PPVO) was administered orally together with 0.5 ml of carbon tetrachloride/animal, with 0.5 ml of physiological sodium chloride solution being injected i.p. Animals in group 3 were again given, by oral administration, a gastric juice-resistant capsule (without PPVO) together with 0.5 ml of carbon tetrachloride animal. In addition, the animals of group 3 were given PPVO D1701 (dose: $5\times10^6$ $TCID_{50}$/animal) in 0.5 ml of water for injection, with this being injected i.p. Group 4 were given, by oral administration, PPVO D1701 (dose: $5\times10^6$ $TCID_{50}$/animal, formulated in a gastric juice-resistant capsule) together with 0.5 ml of carbon tetrachloride. The animals in group 4 were also given 0.5 ml of sterile sodium chloride solution, which was injected i.p.

After 48 hours, the livers were removed and the α-smooth muscle actin (α-SMA)-positive centrilobular area was determined histochemically, for each animal, as a percentage of the total area measured in representative tissue sections (Johnson S J, Hines J E, Burt A D. Phenotypic modulation of perisinusoidal cells following acute liver injury: a quantitative analysis. Int. J Exp. Path. 1992; 73: 765–772). This value is a measure of the transformation of the liver stellate cells.

Two experimental series were carried out in accordance with the above description. The experimental results of the first experimental series are reproduced in Table 3 while the results of the $2^{nd}$ experimental series are reproduced in Table 4.

In experimental series 1, the proportion of the α-SMA-positive centrilobular area in the liver tissue of animals which were given PPVO D1701 by i.p. administration (group 3) was inexplicably (and contrary to the remainder of the experimental experience) higher than in animals which did not receive any PPVO. For this reason, experimental series 2 was carried out as a repeat experiment.

In both experimental series, an approx. 50% inhibition of transformation, as compared with the control group (in each case group 2), was observed, in a concordant and surprising manner, following oral administration of PPVO D1701 (in each case group 4). In the $2^{nd}$ experimental series, the inhibition of transformation following oral administration of PPVO D1701 (group 4) is of a similar magnitude to that observed when PPVO D1701 is administered peritoneally (group 3).

It can be deduced from these results that PPVO also displays its antifibrotic effect following oral administration.

TABLE 1

Influence of Baypamun ® on serum parameters of liver status and indicators of an intoxication

|  | ALT U/l | AST U/l | AP U/l | GGT U/l | GLDH U/l | TBIL μmol/l | EROD nmol g × min |
|---|---|---|---|---|---|---|---|
| Control | 49.1 | 45.7 | 162.8 | 0.8 | 12.5 | 1.6 | 0.30 |
| SEM | 3.7 | 8.7 | 14.76 | 0.2 | 7.9 | 0.2 | 0.02 |
| Carbon tetrachloride | 95.6 | 92.4 | 392.7 | 6.1 | 37.1 | 2.9 | 0.15 |
| SEM | 14.7 | 14.1 | 43.0 | 1.3 | 14.8 | 0.3 | 0.01 |
| Ct + Baypamun ® | 72.0 | 65.9 | 329.5 | 4.5 | 18.2 | 1.9 | 0.17 |
| SEM | 9.9 | 9.1 | 26.9 | 0.8 | 4.0 | 0.2 | 0.03 |

ALT: alanine aminotransferase
AST: aspartate aminotransferase
AP: alkaline phosphatase
GGT: γ-glutamyl transferase
GLDH: glutamate dehydrogenase
TBIL: total bilirubin
EROD: 7-ethoxyresorufin deethylase

TABLE 2

Influence of Baypamun ®

| on liver α-tocopherol | α-Tocopherol nmol/g of tissue |
|---|---|
| Control | 73.1 |
| SEM | 2.2 |
| Carbon tetrachloride | 35.7 |
| SEM | 2.3 |
| C.t + Baypamun ® | 38.5 |
| SEM | 6.1 |

TABLE 3

Influence of PPVO, following intraperitoneal or oral administration, on the transformation of liver stellate cells following the administration of a fibrogenic dose of carbon tetrachloride. (Experimental series 1)

| Fibrosis | Administration | DOSE | α-SMA (%) |
|---|---|---|---|
| Group 1 Intact | empty capsule orally + water for injection i.p. | — | 0.28 ± 0.04 |
| Group 2 Carbon tetrachloride | empty capsule orally + water for injection i.p. | — | 2.76 ± 0.79 |

TABLE 3-continued

Influence of PPVO, following intraperitoneal or oral administration, on the transformation of liver stellate cells following the administration of a fibrogenic dose of carbon tetrachloride. (Experimental series 1)

| Fibrosis | Administration | DOSE | α-SMA (%) |
|---|---|---|---|
| Group 3 Carbon tetrachloride | PPVO in water for injection i.p. + empty capsule orally | $5 \times 10^6$ TCID$_{50}$/animal | 5.05 ± 2.00 |
| Group 4 Carbon tetrachloride | PPVO in capsule, orally + water for injection i.p. | $5 \times 10^6$ TCID$_{50}$/animal | 1.46 ± 0.34 |

TABLE 4

Influence of PPVO, following intraperitoneal or oral administration, on the transformation of liver stellate cells following administration of a fibrogenic dose of carbon tetrachloride. (experimental series 2)

| Fibrosis | Administration | DOSE | α-SMA (%) |
|---|---|---|---|
| Intact Group 1 | empty capsule orally + water for injection i.p. | — | 0.20 ± 0.04 |
| Carbon tetrachloride Group 2 | empty capsule orally + water for injection i.p. | — | 3.18 ± 0.56 |
| Carbon tetrachloride Group 3 | PPVO in water for injection i.p. + empty capsule orally | $5 \times 10^6$ TCID$_{50}$/animal | 1.22 ± 0.35 |
| Carbon tetrachloride Group 4 | PPVO in capsule orally + water for injection i.p. | $5 \times 10^6$ TCID$_{50}$/animal | 1.55 ± 0.34 |

The Parapox Virus NZ-2 used here as an example has been deposited with the European collection of Cell Cultures, Centre for Applied Microbiology and Research, Porton Down, Salisbury, Wiltshire, SP4 OJG, United Kingdom on Jul. 10, 2001. The number of the deposit is 01071006.

What is claimed is:

1. A method of treating organ fibroses in humans, comprising administering to a human an effective amount of an isolate of an inactivated parapoxvirus.

2. The method of claim 1, wherein said parapoxvirus is selected from the strains D 1701, orf-11, Greek orf strain 176, Greek orf strain 155 and the New Zealand (NZ) strains.

3. The method of claim 2, wherein said New Zealand (NZ) strains are selected from the strains NZ2, NZ7 and NZ10.

4. The method of claim 1, wherein said parapoxvirus have been modified by passaging or adaptation to suitable cells.

5. The method of claim 1, wherein said isolate of parapoxvirus comprises parts or fragments of the virus obtainable by means of sonication.

6. The method of claim 1, comprising administering said isolate of a parapoxvirus in combination with other remedies.

7. The method of claim 2, comprising administering *Parapox ovis* D 1701.

8. The method of claim 4, wherein said suitable cells are selected from human cells WI-38 and MRC-5, bovine cells BK-K13A47/Reg and MDBK, and ovine cells MDOK.

9. The method of claim 5, wherein said parts of the virus are genomic or subgenomic fragments expressed with the aid of a vector in a suitable system.

10. The method of claim 9, wherein said vector is vaccinia virus and said suitable system is a fibroblast cell culture.

11. The method of claim 5, wherein said fragments are fractions obtained by biochemical purification of expressed or physically disrupted viral particles.

12. The method of claim 11, wherein said biochemical purification is chromatography.

* * * * *